United States Patent [19]

Suzukamo et al.

[11] Patent Number: 4,877,918
[45] Date of Patent: Oct. 31, 1989

[54] PROCESS FOR PREPARING INTERNAL OLEFINS

[75] Inventors: Gohfu Suzukamo, Ibaraki; Masami Fukao, Shiga, both of Japan

[73] Assignee: Sumitomo Chemical Company, Ltd., Osaka, Japan

[21] Appl. No.: 232,231

[22] Filed: Aug. 15, 1988

[30] Foreign Application Priority Data

Dec. 16, 1987 [JP] Japan .................... 62-319294

[51] Int. Cl.$^4$ .................... C07C 5/23; C07C 5/25
[52] U.S. Cl. ...................................... 585/664
[58] Field of Search .............................. 585/664

[56] References Cited

U.S. PATENT DOCUMENTS

| | | | |
|---|---|---|---|
| 2,361,613 | 10/1944 | Drennan | 585/664 |
| 3,201,493 | 8/1965 | Meisinger | 585/664 |
| 3,204,009 | 8/1965 | Keith | 585/664 |
| 3,501,395 | 3/1970 | Miale | 585/664 |
| 4,205,192 | 5/1980 | Harada | 585/363 |

FOREIGN PATENT DOCUMENTS

| | | | |
|---|---|---|---|
| 687196 | 5/1964 | Canada | 585/664 |
| 0219637 | 4/1987 | European Pat. Off. | |
| 769324 | 7/1970 | France . | |
| 1008964 | 7/1962 | United Kingdom | 585/664 |

*Primary Examiner*—H. M. S. Sneed
*Assistant Examiner*—E. D. Irzinski
*Attorney, Agent, or Firm*—Birch, Stewart, Kolasch & Birch

[57] ABSTRACT

A process for isomerizing an olefin to an internal olefin in the presence of a solid base which is obtainable by heating an alkali metal hydride and alumina, wherein the alumina has been pretreated with at least one salt selected from the group consisting of alkali metal carbonates and alkali metal aluminates, in an atmosphere of an inert gas at a temperature of 200 to 450° C.

23 Claims, No Drawings

PROCESS FOR PREPARING INTERNAL OLEFINS

BACKGROUND OF THE INVENTION

1. Field of the Invention

The present invention relates to a process for preparing internal olefins. More particularly, it relates to a process for preparing a stable internal olefin by isomerizing a less stable olefin in the presence of a specific catalyst.

2. Description of the Related Art

Various processes are known for isomerizing an olefin to a more stable internal olefin. However, the conventionally known method have various disadvantages such as decomposition of the olefin, formation of undesired polymers from the olefin, and random products formed from the olefin, which are economically unfavorable.

As a catalyst for such isomerization, a liquid base such as a mixture of an alkali metal hydroxide and an aprotic organic solvent, a mixture of an alkali metal amide and an amine, or a mixture of an organic alkali metal compound and an aliphatic amine are known. However, such liquid base has an insufficient catalytic activity on the isomerization of olefin so that expensive agents must be used in a large amount. In addition, it is complicated to recover the component agents of the catalyst from a reaction mass so that not only is a troublesome recovering step necessary but also a large amount of energy is consumed.

As a solid catalyst for isomerization of an olefin, an alkali metal dispersed on a carrier with a large surface area (e.g., activated carbon, silica gel, alumina and the like) is known (cf. J. Am. Chem. Soc., 82, 387 (1960)). However, this catalyst, which comprises alkali metal finely dispersed on the carrier, has unsatisfactory handleability and is less safe since it ignites and loses its activity upon contact with air. Further, this dispersion type catalyst exhibits unsatisfactory isomerization activity.

The present inventors have proposed a solid base which is prepared from alumina, an alkali metal hydroxide and an alkali metal or from water-containing alumina and an alkali metal. The solid base has more excellent isomerization activity and a higher stability to air than the alkali metal dispersion catalyst (cf. Japanese Patent Publication Nos. 3274/1975 and 21378/1982 and U.S. Pat. Nos. 3,808,152, 3,897,509 and 3,928,485). However, such a solid base is still unsatisfactory since an alkali metal should be used for its preparation and its catalytic activity is not necessarily high enough.

Also known is the use of a base catalyst comprising an alkali metal hydride carried on a carrier with a catalytic aid such as ammonia or hydrazine (cf. Japanese Patent Kokai Publication Nos. 121758/1978 and 134736/1984 and U.S. Pat. No. 4,205,192). Since the alkali metal hydride can act as a catalyst in the presence of the catalytic aid such as ammonia or hydrazine, it has some drawbacks in that a purification apparatus for separating and removing the catalytic aid is required and that the catalytic reaction is troublesome due to the use of the catalytic aid.

SUMMARY OF THE INVENTION

An object of the present invention is to provide a process for preparing a more stable internal olefin by the use of an isomerization catalyst having high catalytic activity in the absence of a catalytic aid.

This and other objects are accomplished by a process for isomerizing an olefin to an internal olefin in the presence of a solid base which is obtainable by heating an alkali metal hydride and alumina, wherein the alumina has been pretreated with at least one salt selected from the group consisting of alkali metal carbonates and alkali metal aluminates, in an atmosphere of an inert gas at a temperature of 200° to 450° C.

DETAILED DESCRIPTION OF THE INVENTION

In the present invention, the alkali metal hydride are hydrides of metals of Group I of the Periodic Table such as lithium hydride, sodium hydride, potassium hydride, rubidium hydride and cesium hydride and mixtures thereof. The alkali metal hydride is used in an amount of 2 to 10% by weight, preferably 4 to 8% by weight based on the weight of alumina.

Examples of the carbonate and aluminate to be used in the pretreatment of alumina are carbonates and aluminates of metals of Group I of the Periodic Table such as lithium, sodium, potassium, rubidium and cesium.

As alumina, various aluminas except $\alpha$-alumina are used. Particularly, alumina with a relatively large surface area such as $\gamma$-, $\chi$- and $\rho$-alumina are preferred in view of the catalytic activity. Water-containing alumina may be used.

Since alumina acts as a carrier as well as a reactant with the alkali metal hydride and the alkali metal carbonate or aluminate to form new bonds an aluminum-containing compound such as kaolin and alumina silicate may be used in place of alumina. However, alumina is preferably used.

The pretreatment of alumina is effected by impregnating alumina with an aqueous solution of the alkali metal carbonate or aluminate followed by calcining. The amount of the alkali metal salt to be impregnated in alumina is from 5 to 30% by weight, preferably from 5 to 20% by weight based on the weight of alumina. The calcining temperature is preferably from 300° to 700° C.

Then, preferred alumina and the alkali metal hydride are heated at a specific temperature in an inert gas atmosphere as described above to prepare the solid base to be used in the process of the present invention. As the inert gas, nitrogen, helium, argon and the like can be used.

In the present invention, the catalytic activity of the solid base are influenced by the temperature at which pretreated alumina and the alkali metal hydride are heated. Therefore, the heating temperature is from 200° to 450° C., preferably from 220° to 400° C., more preferably from 250° to 400° C.

By preparing the solid base at such specific temperature, the solid base has very high catalytic activity which is not achieved by the conventional solid base, so that it can catalyze isomerization reactions in a smaller amount.

Although the heating time varies with other reaction conditions such as temperature, it is generally from 15 minutes to 10 hours.

During heating the pretreated alumina and the alkali metal hydride, new active species may be formed, so that the catalytic activity of the solid base according to the present invention is much higher than the conventional catalysts and can catalyze the objective reaction in the absence of the aid such as ammonia or hydrazine.

In the process of the present invention, the olefin is isomerized to the more stable internal olefin in the presence of such solid base.

Examples of olefins to be isomerized are terminal olefins such as unsaturated aliphatic compounds (e.g. 1-butene, 1-pentene, 1-hexene, 1-heptene, 1-nonene, 1-decene, 2-methyl-1-butene, 3-methyl-1-butene, 4-methyl-1-pentene, 3-methyl-1-pentene, 2-methyl-1-pentene, 2,3-dimethyl-1-butene, etc.), aromatic compounds (e.g. allylbenzene, allyltoluene, etc.), bridged ring compounds (2-isopropenylnorbornane, 5-isopropenyl-2-norbornene, 5-vinyl-2-norbornene, 6-methyl-5-vinylnorbornen, etc.), cyclic compounds (e.g. methylenecyclopentane, methylenecyclohexane, etc.), diolefins (e.g. 1,4-pentadiene, 1,5-hexadiene, 2,5-dimethyl-1,4-hexadiene, 2,5-dimethyl-1,5-hexadiene, etc.); and compounds having an internal double bond which can be isomerized to a more stable position (e.g. 4-methyl-2-pentene, 5-(2-propenyl)-2-norbornene, etc.).

In the preparation of internal olefin, the amount of solid base catalyst to be used is from 1/3,000 to 1/20, preferably from 1/2,000 to 1/100 part by weight per part of the raw material olefin. It is not necessarily required to heat the reaction system since isomerization proceeds at room temperature, although the reaction system may be heated. Usually, the isomerization temperature is from −30 to +120° C., preferably from −10 to +100° C.

Optionally, an inert solvent may be used. Examples of the inert solvent are hydrocarbons such as pentane, hexane, heptane and dodecane. Preferably, the isomerization is carried out in the absence of the solvent or in the presence of a solvent which can be a solvent in a subsequent step, since highly pure internal olefins are recovered by only the removal of the catalyst.

The process according to the present invention is carried out batchwise or continuously. Preferably, the raw material olefin is pretreated with a drying agent such as alumina. For assuring the complete and safe proceeding of reaction, the isomerization may be carried out in an atmosphere of an inert gas such as nitrogen, helium and argon.

The isomerization product is usually analyzed by such method as gas chromatography and isolated from the catalyst by a conventional manner such as filtration or decantation.

According to the present invention, the solid base is prepared by using the alkali metal hydride which is easily handled, and moreover it has high catalytic activity without using ammonia or hydrazine. Thus, a small amount of the solid base can effectively isomerize the olefin to give the internal olefin with a high yield without the formation of by-products such as polymerized materials.

Practically and presently preferred embodiments of the present invention will be illustrated by following examples.

REFERENCE EXAMPLE 1

To a mixture of sodium aluminate (23.5 g) and water (200 ml) in a 300 ml flask, γ-alumina (109 g) was added. Then, the mixture was dried with removing water at 60° C. under reduced pressure while stirring to obtain a solid material (131.8 g).

REFERENCE EXAMPLE 2

In the same manner as in Reference Example 1 but using potassium carbonate (15.0 g) in place of sodium aluminate, a solid material (123.3 g) was prepared.

REFERENCE EXAMPLE 3

To a 100 ml flask, the solid material (25.0 g) obtained in Reference Example 1 was added, heated to 450° C. while stirring in a nitrogen stream for 2 hours. After cooling, sodium hydride (1.1 g) was added, and the mixture was heated to 350° C. while stirring and kept at the same temperature while stirring for 1 (one) hour followed by cooling to obtain a solid base (24.1 g).

REFERENCE EXAMPLES 4 TO 11

In the same manner as in Reference Example 3 but using materials shown in Table 1, a solid base was prepared.

TABLE 1

| Reference No. | Alumina Reference No. | Amount (g) | Pretreatment conditions Temp. (°C.) | Time (hrs) | Alkali metal hydride Hydride | Amount (g) | Reaction conditions Temp. (°C.) | Time (hrs) |
|---|---|---|---|---|---|---|---|---|
| 4 | 1 | 25.0 | 450 | 2 | NaH | 1.1 | 250 | 3 |
| 5 | 1 | ↑ | ↑ | ↑ | KH | 1.8 | 300 | 1 |
| 6 | 2 | ↑ | ↑ | 4 | NaH | 1.1 | 350 | 1 |
| 7 | 2 | ↑ | ↑ | ↑ | ↑ | ↑ | 250 | 3 |
| 8 | 1 | ↑ | ↑ | 2 | ↑ | ↑ | 170 | 1 |
| 9 | 1 | ↑ | ↑ | ↑ | ↑ | ↑ | 510 | 1 |
| 10 | 2 | ↑ | ↑ | 4 | ↑ | ↑ | 170 | 1 |
| 11 | 2 | ↑ | ↑ | ↑ | ↑ | ↑ | 510 | 1 |
| 12 | 1 | ↑ | ↑ | 2 | ↑ | ↑ | 400 | 1 |
| 13 | 2 | ↑ | ↑ | 4 | ↑ | ↑ | 400 | 1 |

EXAMPLE 1

To a 150 ml flask in nitrogen atmosphere, the solid base prepared in Reference Example 3 (0.21 g) and then 5-vinyl-2-norbornene (hereinafter referred to as "VNB") (purity, 99.9%) (76.0 g) were added and the resultant mixture was stirred at a temperature of 15°-20° C. for 10 hours. Thereafter, the catalyst was filtered off to obtain a reaction mixture (75.4 g). Gas chromatographic analysis of the mixture revealed that 99.4% of 5-ethylidene-2-norbornene (hereinafter referred to as "ENB") and 0.5% of VNB were contained in the product.

EXAMPLES 2-7 AND COMPARATIVE EXAMPLES 1-4

In the same manner as in Example 1 but using the solid base and reaction conditions shown in Table 2, VNB was isomerized to ENB. The results are also shown in Table 2.

TABLE 2

| Example No. | Solid base Ref. Ex. No. | Grams | Amount of VNB (g) | Reaction conditions Temp. (°C.) | Time (hrs) | Reaction results VNB (%) | ENB (%) |
| --- | --- | --- | --- | --- | --- | --- | --- |
| 2 | 4 | 0.25 | 33.0 | 15–20 | 10 | 0.7 | 99.2 |
| 3 | 5 | 0.22 | 65.8 | ↑ | 6 | 0.3 | 99.6 |
| 4 | 12 | 0.25 | 48.5 | ↑ | 10 | 0.4 | 99.5 |
| Comp. 1 | 8 | 0.30 | 15.0 | ↑ | 24 | 99.8 | 0.1 |
| Comp. 2 | 9 | 0.30 | 15.0 | ↑ | 20 | 13.7 | 86.2 |
| 5 | 6 | 0.20 | 69.4 | ↑ | 10 | 0.5 | 99.4 |
| 6 | 7 | 0.25 | 33.8 | ↑ | 10 | 0.4 | 99.5 |
| 7 | 13 | 0.24 | 45.3 | ↑ | 10 | 0.4 | 99.5 |
| Comp. 3 | 10 | 0.30 | 15.0 | ↑ | 24 | 99.7 | 0.2 |
| Comp. 4 | 11 | 0.30 | 15.0 | ↑ | 20 | 6.1 | 93.8 |

EXAMPLE 8

A tube of 5 mm in inner diameter and 100 mm in length equipped with an outer jacket was filled with the solid base prepared in Reference Example 3 (0.96 g) in nitrogen atmosphere. VNB (purity, 99.9%) was flowed from the upper end of the tube at a flow rate of 3.4 g/hr. with circulating cooling water kept at 15° to 20° C. in the jacket.

The effluent from the lower end of the tube was analyzed. The composition of the effluent was as follows:

| Time (hrs.) | VNB (%) | ENB (%) |
| --- | --- | --- |
| 15 | 0.3 | 99.5 |
| 25 | 0.3 | 99.5 |
| 35 | 0.3 | 99.5 |
| 45 | 0.3 | 99.5 |

The total amount of effluent was 151.7 g and an average purity of ENB was 99.5%.

EXAMPLE 9

In a 100 ml flask in nitrogen atmosphere, the solid base prepared in Reference Example 4 (0.25 g) and then 4-methyl-1-pentene (17.5 g) were charged and the resultant mixture was stirred at a temperature of 15°–20° C. for 16 hours. Gas chromatographic analysis of the resulting reaction mixture revealed that 90.5% of 2-methyl-2-pentene, 8.9% of 4-methyl-2-pentene and 0.4% of 4-methyl-1-pentene were contained in the mixture.

EXAMPLE 10

To a 200 ml flask in nitrogen atmosphere, the solid base prepared in Reference Example 5 (0.25 g) and then 4-methyl-1-pentene (36.2 g) were added and stirred at a temperature of 15°–20° C. for 8 hours. Gas chromatographic analysis of the resulting reaction mixture revealed that 90.2% of 2-methyl-2-pentene, 9.4% of 4-methyl-2-pentene and 0.4% of 4-methyl-1-pentene were contained in the mixture.

COMPARATIVE EXAMPLE 5

To a 100 ml flask in nitrogen atmosphere, the solid base prepared in Reference Example 8 (0.03 g) and then 4-methyl-1-pentene (6.0 g) were added and stirred at temperature of 15°–20° C. for 8 hours. Gas chromatographic analysis of the resulting reaction mixture revealed that 90.7% of 4-methyl-1-pentene, 5.8% of 4-methyl-2-pentene and 3.3% of 2-methyl-2-pentene were contained in the mixture.

EXAMPLE 11

To a 100 ml flask in nitrogen atmosphere, the solid base prepared in Reference Example 7 (0.25 g) and then 4-methyl-1-pentene (18.0 g) were added and the resultant mixture was stirred at a temperature of 15°–20° C. for 16 hours. Gas chromatographic analysis of the product revealed that 90.4% of 2-methyl-2-pentene, 8.9% of 4-methyl-2-pentene and 0.5% of 4-methyl-1-pentene were contained in the product.

EXAMPLE 12

To a 200 ml flask in nitrogen atmosphere, the solid base prepared in Reference Example 6 (0.25 g) and then 4-methyl-1-pentene (36.3 g) were added and the resultant mixture was stirred at a temperature of 15°–20° C. for 8 hours. Gas chromatographic analysis of the product revealed that 90.6% of 2-methyl-2-pentene, 8.8% of 4-methyl-2-pentene and 0.4% of 4-methyl-1-pentene were contained in the product.

COMPARATIVE EXAMPLE 6

To a 100 ml flask in nitrogen atmosphere, the solid base prepared in Reference Example 10 (0.31 g) and then 4-methyl-1-pentene (6.0 g) were added and the resultant mixture was stirred at a temperature of 15°–20° C. for 48 hours. Gas chromatographic analysis of the product revealed that 89.3% of 4-methyl-1-pentene, 6.7% of 4-methyl-2-pentene and 3.9% of 2-methyl-2-pentene were contained in the product.

What is claimed is:

1. A process for isomerizing an olefin to an internal olefin in the presence of a solid base which comprises:
    pretreating alumina with at least one salt selected from the group consisting of alkali metal carbonates and alkali metal aluminates so as to form pretreated alumina,
    forming a solid base by heating an alkali metal hydride and said pretreated alumina in an atmosphere of an inert gas at a temperature of 200° to 450° C., and
    isomerizing an unprocessed olefin to an internal olefin in the presence of said solid base at an isomerization temperature of from −30° to +120° C., wherein said solid base is present in an amount of from 1/3000 to 1/20 part by weight of unprocessed olefin.

2. The process according to claim 1, wherein the alumina is pretreated with an alkali metal carbonate.

3. The process according to claim 2, wherein the alkali metal hydride and the pretreated alumina are heated to form a solid base at a temperature of 250° to 400° C.

4. The process according to claim 2, wherein the alkali metal hydride is selected from the group consisting of sodium hydride, potassium hydride and mixtures thereof.

5. The process according to claim 2, wherein the alkali metal hydride is used in an amount of 2 to 10% by weight based on the weight of alumina.

6. The process according to claim 2, wherein the alkali metal carbonate is selected from the group consisting of lithium carbonate, sodium carbonate, potassium carbonate, rubidium carbonate and cesium carbonate and mixtures thereof.

7. The process according to claim 2, wherein the alumina is pretreated by impregnating the alumina with an aqueous solution of an alkali metal carbonate and sintering the impregnated alumina to form the pretreated alumina.

8. The process according to claim 7, wherein the impregnated alumina is calcined at a temperature of 300° to 700° C.

9. The process according to claim 6, wherein the alumina is selected from the group consisting of $\gamma$-alumina, $\chi$-alumina and $\rho$-alumina.

10. The process according to claim 7, wherein the amount of the impregnated alkali metal carbonate is from 5 to 30% by weight based on the weight of the alumina.

11. The process according to claim 1, wherein the alumina is pretreated with an alkali metal aluminate.

12. The process according to claim 11, wherein the alkali metal hydride and the pretreated alumina are heated to form a solid base at a temperature of 250° to 400° C.

13. The process according to claim 11, wherein the alkali metal hydride is selected from the group consisting of sodium hydride, potassium hydride and mixtures thereof.

14. The process according to claim 11, wherein the alkali metal hydride is used in an amount of 2 to 10% by weight based on the weight of alumina.

15. The process according to claim 11, wherein the alkali metal aluminate is selected from the group consisting of lithium aluminate, sodium aluminate, potassium aluminate, rubidium aluminate and cesium aluminate and mixtures thereof.

16. The process according to claim 11, wherein the alumina is pretreated by impregnating the alumina with an aqueous solution of an alkali metal aluminate and sintering the impregnated alumina to form the pretreated alumina.

17. The process according to claim 16, wherein the impregnated alumina is calcined at a temperature of 300° to 700° C.

18. The process according to claim 15, wherein the alumina is selected from the group consisting of $\gamma$-alumina, $\chi$-alumina and $\rho$-alumina.

19. The process according to claim 16, wherein the amount of the impregnated alkali metal aluminate is from 5 to 30% by weight based on the weight of the alumina.

20. The process according to claim 7, wherein the amount of the impregnated alkali metal carbonate is from 5 to 20% by weight based on the weight of the alumina.

21. The process according to claim 16, wherein the amount of the impregnated alkali metal aluminate is from 5 to 20% by weight based on the weight of the alumina.

22. The process according to claim 1, wherein said isomerization temperature is from $-10°$ to $+100°$ C. and said solid base is present in an amount from 1/2000 to 1/100 part by weight of unprocessed olefin.

23. The process according to claim 3, wherein the alkali metal hydride is used in an amount of 4 to 8% by weight based on the weight of the alumina, said isomerization temperature is from $-10°$ to $+100°$ C., and said solid base is present in an amount from 1/2000 to 1/100 part by weight of unprocessed olefin.

* * * * *